United States Patent
Cauwet-Martin et al.

(10) Patent No.: US 6,403,073 B1
(45) Date of Patent: Jun. 11, 2002

(54) COMPOSITIONS FOR TREATING KERATINIC MATERIALS CONTAINING THE ASSOCIATION OF A POLYAMPHOLYTE POLYMER AND A NON-VOLATILE AND WATER INSOLUBLE ORGANOPOLYSILOXANE

(75) Inventors: Daniéle Cauwet-Martin, Paris; Bertrand Lion, Livry Gargan; Jean Mondet, Aulnay sous Bois, all of (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/180,762

(22) PCT Filed: May 5, 1997

(86) PCT No.: PCT/FR97/00792

§ 371 (c)(1),
(2), (4) Date: Jan. 29, 1999

(87) PCT Pub. No.: WO97/42931

PCT Pub. Date: Nov. 20, 1997

(30) Foreign Application Priority Data

May 13, 1996 (FR) .............................. 96 05917

(51) Int. Cl.$^7$ ................................................ A61K 7/06
(52) U.S. Cl. ...................................... 424/70.1; 424/407
(58) Field of Search .................... 424/70.1, 401

(56) References Cited

U.S. PATENT DOCUMENTS

| | | | |
|---|---|---|---|
| 2,528,378 A | 10/1950 | Mannheimer | 260/309.6 |
| 2,781,354 A | 2/1957 | Mannheimer | 260/309.6 |
| 4,693,935 A | 9/1987 | Mazurek | 428/352 |
| 4,728,571 A | 3/1988 | Clemens et al. | 428/352 |
| 4,972,037 A | 11/1990 | Garbe et al. | 526/245 |
| 4,994,088 A * | 2/1991 | Ando et al. | 8/426 |
| 5,068,278 A * | 11/1991 | Peiffer et al. | 524/547 |
| 5,169,622 A * | 12/1992 | Kopolow et al. | 424/47 |
| 5,275,755 A | 1/1994 | Sebag et al. | 252/174.15 |
| 5,609,862 A | 3/1997 | Chen et al. | 424/70.11 |
| 5,679,114 A * | 10/1997 | Haning et al. | 8/405 |

FOREIGN PATENT DOCUMENTS

| | | |
|---|---|---|
| EP | 0 185 507 | 6/1986 |
| EP | 0 342 834 | 11/1989 |
| EP | 0 412 704 | 2/1991 |
| EP | 0 412 707 | 2/1991 |
| EP | 0 492 657 | 7/1992 |
| EP | 0 582 152 | 2/1994 |
| FR | 2 589 476 | 5/1987 |
| FR | 2 641 185 | 7/1990 |
| FR | 2 709 955 | 3/1995 |
| JP | 63-135319 | 6/1988 |
| JP | 63-313712 | 12/1988 |
| JP | 63-316713 | 12/1988 |
| JP | 1-128915 | 5/1989 |
| JP | 01-190619 | 7/1989 |
| JP | 01-190620 | 7/1989 |
| JP | 02-111711 | 4/1990 |
| JP | 03-291210 | 12/1991 |
| JP | 04-187624 | 7/1992 |
| JP | 04-226908 | 8/1992 |
| JP | 05-092911 | 4/1993 |
| JP | 05-246828 | 9/1993 |
| JP | 06-172144 | 6/1994 |
| JP | 7-15115 | 1/1995 |
| WO | WO 93/23009 | 11/1993 |
| WO | WO 93/23446 | 11/1993 |
| WO | WO 95/00578 | 1/1995 |
| WO | WO 95/03776 | 2/1995 |

OTHER PUBLICATIONS

Encyclopedia of Polymer Science and Engineering, Second Edition, vol. 17, pp. 517–521 (John Wiley & Sons).

Jean–Marc Corpart et al., "Aqueous Solution Properties of Ampholytic Copolymers Prepared in Microemulsions", Macromolecules, vol. 26., No. 6, 1993, pp. 1333–1343.

Igor Lacik et al., "Compositional heterogeneity effects in hydrophobically associating water–soluble polymers prepared by icellar copolymerization", Polymer, vol. 36, No. 16, 1995, pp. 3197–3211.

M.R. Porter, Handbook of Surfactants, Blackie & Son (Glasgow and London) 1991, pp. 116–178.

J.C. Salamone et al., "Polymerization of Ion–Pair Comonomers of Related Structures", J. Macromol. Sci. Chem., A22 (5–7), 1985, pp. 653–664.

English Language Derwent Abstract of FR 2 589 476.
English Language Derwent Abstract of FR 2 641 185.
English Language Derwent Abstract of FR 2 709 955.
English Language Derwent Abstract of JP 7–15115.
Patent Abstracts of Japan, vol. 13, No. 379 (JP 1–128915).

* cited by examiner

Primary Examiner—Jose' G. Dees
Assistant Examiner—Konata M George
(74) Attorney, Agent, or Firm—Finnegan, Henderson, Farabow, Garrett & Dunner, L.L.P.

(57) ABSTRACT

The invention features a composition for treating keratin materials in particular human hair, containing in a cosmetically and dermatologically acceptable aqueous medium at least: a) a polyampholyte polymer comprising in the chain or in a lateral position relative to the chain, equimolar or practically equimolar amounts of negative charges and positive charges; the said polymer being water-insoluble at a concentration of 0.1% by weight or above and at 20° C.; b) a non-volatile, water-insoluble organopolysiloxyne of a viscosity higher than $3.10^{-5}$ m$^2$/s (300 centistokes).

50 Claims, No Drawings

COMPOSITIONS FOR TREATING KERATINIC MATERIALS CONTAINING THE ASSOCIATION OF A POLYAMPHOLYTE POLYMER AND A NON-VOLATILE AND WATER INSOLUBLE ORGANOPOLYSILOXANE

The present invention relates to novel compositions for treating keratin substances, in particular the hair, containing a combination of a polyampholytic polymer and a non-volatile, water-insoluble polyorganosiloxane, as well as to uses thereof.

Hair conditioners which provide additional cosmetic effects after application and rinsing, such as softness, flexibility, good disentangling, a sheen effect and/or a styling effect, have been sought in recent years in the field of shampoos and conditioners.

It is known in the prior art that silicones are cosmetic products which are particularly desired in hair formulations for their hair-conditioning properties, their softening and disentangling properties and for the sheen effect they provide. When they are used in rinse-out hair compositions, these ingredients have the drawback of being difficult to deposit on the hair and to do so in a non-uniform manner when applied and after rinsing, and of not being able to give the hair the desired effects intrinsic to silicones.

Patent application JP 7-15115 and U.S. Pat. No. 4,994,088 have envisaged shampoo compositions based on polyampholytic polymers. These are specific polyelectrolytic polymers which have equimolar amounts (or virtually equimolar amounts) of negative charges and positive charges. These polymers are generally insoluble in water and generally have the characteristic of being deposited on the hair by dilution and precipitation during the rinsing and fixing step and/or of maintaining the hair after the shampoo has been applied.

The Applicant has discovered that by combining these polyampholytic polymers with non-volatile, water-insoluble polyorganosiloxanes with a viscosity which will be defined later, it is possible, surprisingly to obtain silicone-based rinse-out hair compositions which do not have the drawbacks mentioned above, giving better cosmetic performance, in particular as regards the feel and the disentangling, as well as good styling properties.

Moreover, the Applicant has discovered, unexpectedly, that by combining the silicones of the invention with polyampholytes, the cosmetic performance of the polyampholyte is improved substantially.

The compositions according to the invention are essentially characterized in that they contain, in a cosmetically and/or dermatologically acceptable aqueous medium, at least:
(a) one non-volatile, water-insoluble polyorganosiloxane with a viscosity of greater than $3\times10^{-5}$ m²/s (300 centistokes);
(b) one polyampholytic polymer containing, in the chain or in a side position relative to the chain, equimolar amounts, or virtually equimolar amounts, of negative charges and positive charges; the said polyampholytic polymer being insoluble in water at a concentration of greater than or equal to 0.1% by weight and at 20° C. and the said polymer being other than betaine homopolymers or copolymers containing a monomer chosen from the group consisting of:
(i) the monomers of the following formula:

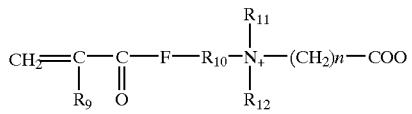

which:
$R_9$, $R_{11}$ and $R_{12}$, which may be identical or different, denote a hydrogen or an alkyl radical;
$R_{10}$ denotes a group $-(CH_2)_n-$ or $-(O-CH_2-CH_2)_m-$; F denotes NH or O; m and n are integers ranging from 1 to 4;
(ii) the monomer of the following formula:

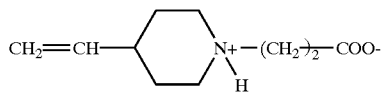

(iii) the monomer of the following formula:

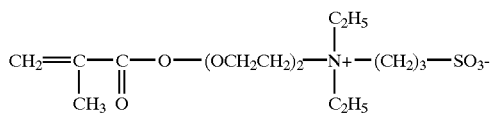

(iv) the monomer of the following formula:

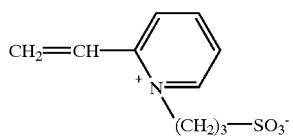

The polyorganopolysiloxanes of the invention preferably have a viscosity of greater than $5\times10^{-5}$ m²/s (500 centistokes) and more particularly of greater than $10\times10^{-5}$ m²/s (1000 centistokes).

Among the polyorganosiloxanes of the invention with a viscosity of greater than $3\times10^{-3}$ m²/s mention may be made of:
(i) polyalkylsiloxanes;
(ii) polyarylsiloxanes;
(iii) polyalkylarylsiloxanes;
(iv) silicone gums;
(v) silicone resins;
(vi) polyorganosiloxanes containing in their general structure one or more organofunctional groups directly attached to the siloxane chain or attached via a hydrocarbon-based radical;
(vii) block copolymers having a polysiloxane-polyoxyalkylene linear block as repeating units;
(viii) grafted silicone polymers containing a non-silicone organic skeleton, consisting of an organic main chain formed from organic monomers not containing silicone, onto which is grafted, within the said chain as well as, optionally, on at least one of its ends, at least one polysiloxane macromonomer;
(ix) grafted silicone polymers containing a polysiloxane skeleton, grafted with non-silicone organic monomers, comprising a polysiloxane main chain onto which is grafted, within the said chain as well as, optionally, on at least one of its ends, at least one organic macromonomer not containing silicone;

(x) or mixtures thereof.

Among the polyalkylsiloxanes, mention may be made mainly of:

linear polydimethylsiloxanes containing trimethylsilyl end groups, such as, for example, and in a non-limiting manner, the Silbione oils of the 70047 series sold by Rhône-Poulenc; the oil 47 V 500 000 from Rhône-Poulenc or certain Viscasil oils from General Electric;

linear polydimethylsiloxanes containing hydroxydimethylsilyl end groups, such as the oils of the 48 V series from Rhône-Poulenc.

In this class of polyalkylsiloxanes, mention may also be made of the polyalkylsiloxanes sold by the company Goldschmidt under the trade names Abilwax 9800 and Abilwax 9801, which are poly($C_1$–$C_{20}$)alkylsiloxanes.

Among the polyalkylarylsiloxanes, mention may be made of linear and branched polydimethylmethylphenylsiloxanes and polydimethyldiphenylsiloxanes, such as the product DC 556 Cosmetic Grade Fluid from Dow Corning.

The silicone gums in accordance with the invention are polyorganosiloxanes with a molecular mass of between 200,000 and 1,000,000, used alone or as a mixture in a solvent chosen from the group consisting of volatile silicones, polydimethylsiloxane oils, polyphenylmethylsiloxane oils, isoparaffins, methylene chloride, pentane, dodecane, tridecane and tetradecane, or mixtures thereof.

Mention is made, for example, of the following compounds:

polydimethylsiloxane,
poly[(dimethylsiloxane)/(methylvinylsiloxane)],
poly[(dimethylsiloxane)/(diphenylsiloxane)],
poly[(dimethylsiloxane)/(phenylmethylsiloxane)],
poly[(dimethylsiloxane)/(diphenylsiloxane)/(methylvinylsiloxane)].

Mention may be made, for example, of the following mixtures:

1) mixtures formed from a polydimethylsiloxane hydroxylated at the end of the chain (Dimethiconol according to the CTFA nomenclature) and from a cyclic polydimethylsiloxane (Cyclomethicone), such as the product Q2 1401 sold by the company Dow Corning;

2) mixtures formed from a polydimethylsiloxane gum with a cyclic silicone, such as the product SF 1214 Silicone Fluid from General Electric, which is an SE 30 gum of molecular weight 500,000 dissolved in SF 1202 Silicone Fluid (decamethylcyclopentasiloxane);

3) mixtures of two polydimethylsiloxanes (PDMS) of different viscosity, in particular a PDMS gum and a PDMS oil, such as the products SF 1236 and CF 1241 from General Electric. The product SF 1236 is a mixture of an SE 30 oil defined above, with a viscosity of 20 $m^2$/s, and of an SF 96 oil with a viscosity of $5\times10^{-5}$ $m^2$/s (15% SE 30 gum and 85% SF 96 oil). The product CF 1241 is a mixture of an SE 30 gum (33%) and of a PDMS (67%) with a viscosity of $10_{-3}$ $m^2$/s.

The silicone resins in accordance with the invention are preferably crosslinked siloxane systems containing the units:

$R_2SiO_{2/2}$, $RSiO_{3/2}$ and $SiO_{4/2}$, in which R denotes a hydrocarbon-based group having 1 to 6 carbon atoms or a phenyl group. Among these products, the ones which are particularly preferred are those in which R denotes a lower alkyl radical or a phenyl radical.

Among these resins, mention may be made of the product sold under the name Dow Corning 593 by Dow Corning or those sold under the name Silicone Fluid SS 4267 by General Electric and which are dimethyl/trimethylpolysiloxanes.

The organomodified polyorganosiloxanes of the invention are polyorganosiloxanes as defined above, containing in their general structure one or more organofunctional groups directly attached to the siloxane chain or attached via a hydrocarbon-based radical.

Mention is made, for example, of polyorganosiloxanes containing:

a) polyethylenoxy and/or polypropylenoxy groups, optionally containing alkyl groups, such as the product known as lauryl methicone copolyol sold under the name Q2 5200 by Dow Corning;

b) (per)fluoro groups, for instance trifluoroalkyl groups such as, for example, those sold by Shin Etsu under the name FL 100;

c) hydroxyacylamino groups such as those described in patent application EP-A-0,342,834;

d) thiol groups;

e) carboxylate groups, such as the products described in European patent EP 185 507 from Chisso Corporation;

f) hydroxyl groups, such as the polyorganopolysiloxanes containing a hydroxyalkyl function, described in French patent application FR 85/16334, and in particular polyorganopolysiloxanes containing a γ-hydroxypropyl function;

g) alkoxy groups containing at least 12 carbon atoms, such as the product Silicone Copolymer F755 from SWS Silicones and the products Abilwax 2428, Abilwax 2434 and Abilwax 2440 from the company Goldschmidt;

i) acyloxyalkyl groups containing at least 12 carbon atoms, such as the polyorganosiloxanes described in French patent application FR 88/17433 and in particular polyorganosiloxanes containing a stearoyloxypropyl function;

j) substituted or unsubstituted amine groups, such as the products GP 7100 from Genesee or the products KF 861, KF 864, X22 380 D and X22 3801 C from Shin Etsu;

k) quaternary ammonium groups;

l) amphoteric or betaine groups;

m) bisulphite groups.

The block copolymers having a polysiloxane-polyoxyalkylene linear block as repeating unit, which are used in the context of the present invention, preferably have the following general formula:

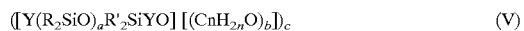

in which

R and R', which may be identical or different, represent a monovalent hydrocarbon-based radical containing no aliphatic unsaturation, n is an integer ranging from 2 to 4, a is an integer greater than or equal to 5, preferably between 5 and 200 and even more particularly between 5 and 100, b is an integer greater than or equal to 4, preferably between 4 and 200 and even more particularly between 5 and 100, c is an integer greater than or equal to 4, preferably between 4 and 1000 and even more particularly between 5 and 300, Y represents a divalent organic group which is linked to the adjacent silicon atom via a carbon-silicon bond and to a polyoxyalkylene block via an oxygen atom, the average molecular weight of each siloxane block is between about 400 and about 10,000, that of each polyoxyalkylene block being between about 300 and about 10,000, the ciloxane blocks represent from about 10% to about 95% of the weight of the block copolymer, the average molecular weight of the block copolymer being at least 3000 and preferably between 5000 and 1,000,000 and even more particularly between 10,000 and 200,000.

R and R' are preferably chosen from the group comprising alkyl radicals such as, for example, the methyl, ethyl, propyl, butyl, pentyl, hexyl, octyl, decyl and dodecyl radicals, aryl radicals such as, for example, phenyl and naphthyl, aralkyl radicals such as, for example, benzyl and phenylethyl, and tolyl, xylyl and cyclohexyl radicals.

Y is preferably —R''—, —R''—CO—, —R''—NHCO—, —R''—NH—CO—NH—R'''—NHCO or —R''—OCONH—R'''—NHCO—, where R'' is a divalent alkylene group such as, for example, ethylene, propylene or butylene, and R''' is a divalent alkylene group or a divalent arylene group such as —C$_6$H$_4$—, —C$_6$H$_4$—C$_6$H$_4$—, —C$_6$H$_4$—CH$_2$—C$_6$H$_4$—, —C$_6$H$_4$—C(CH$_3$)$_2$—C$_6$H$_4$—.

Even more preferably, Y represents a divalent alkylene radical, more particularly the —CH$_2$—CH$_2$—CH$_2$ radical or the C$_4$H$_8$ radical.

The preparation of the block copolymers used in the context of the present invention is described in European application EP 0,492,657 A1, the teaching of which is included by way of reference in the present description.

The preferred polysiloxane-polyoxyalkylene linear block copolymers according to the invention are chosen from those of formula:

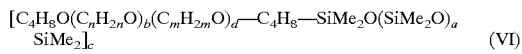

where Me represents methyl, n and m are integers ranging from 2 to 4, a is an integer greater than or equal to 4, preferably between 5 and 200, b and d are integers greater than or equal to 0, preferably between 4 and 200, b+d is greater than or equal to 4, preferably between 4 and 200, and c is an integer greater than or equal to 4, preferably between 4 and 1000.

Among these copolymers, the ones more particularly used are those having a repeating unit of formula:

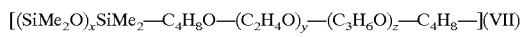

where x is a number between 5 and 15 (limits included), y is a number between 15 and 30 (limits included), and z is a number between 20 and 40 (limits included).

Among these polymers, the ones more particularly used are those in which the siloxane/polyoxyalkylene weight ratio is about 20 and the polyoxyethylene/polyoxypropylene weight ratio is about 65/35.

Polymers can also be chosen in which the repeating unit is of formula (VI) and whose siloxane/polyoxyalkylene weight ratio is about 75 and whose polyoxyethylene/polyoxypropylene weight ratio is about 50/50, polymers whose siloxane/polyoxyalkylene weight ratio is about 35 and whose polyoxyethylene/polyoxypropylene weight ratio is about 100/0, and polymers whose siloxane/polyoxyalkylene weight ratio is about 30 and whose polyoxyethylene/polyoxypropylene weight ratio is about 0/100.

According to a particular embodiment of the invention, the block copolymer is chosen from the following copolymers:

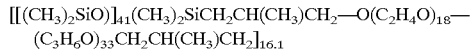

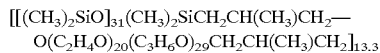

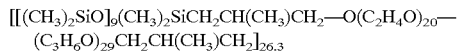

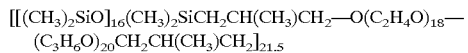

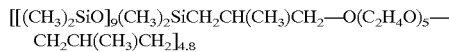

The polymers containing a non-silicone organic skeleton grafted with monomers containing a polysiloxane, in accordance with the invention, are preferably chosen from those described in U.S. Pat. Nos. 4,693,935, 4,728,571 and 4,972,037 and patent applications EP-A-0,412,704, EP-A-0,412,707, EP-A-0,640,105 and WO 95/00578, the teachings of which are included in their entirety in the present description by way of non-limiting references. They are copolymers obtained by radical polymerization from monomers containing ethylenic unsaturation and from silicone macromers having a vinyl end group, or alternatively copolymers obtained by reaction of a polyolefin comprising functionalized groups and of a polysiloxane macromer having an end function which is reactive with the said functionalized groups.

Examples of polymers containing a polysiloxane skeleton grafted with non-silicone organic monomers, which are suitable for carrying out the present invention, as well as the particular method for preparing them, are described in particular in patent applications EP-A-0,582,152, WO 93/23009 and WO 95/03776, the teachings of which are included in their entirety in the present description by way of non-limiting references.

The polyorganosiloxanes of the invention are present in the compositions in proportions preferably ranging from 0.001 to 20% by weight, and preferably from 0.01 to 10% by weight, relative to the total weight of the composition.

The "polyampholytic" polymers corresponding to the definition given above, in accordance with the invention, have an overall charge close to zero at a pH in the region of 7.

These polymers are generally insoluble in water at a concentration greater than or equal to 0.1% by weight and at 20° C. Some of them can dissolve in aqueous electrolyte solutions, preferably containing inorganic electrolytes. Some of them can also dissolve directly in a surfactant-based washing base, others dissolve in a washing base in the additional presence of electrolytes. The solubility of these polymers in the aqueous medium will depend on the structure of the polyampholyte chosen. In general, these polymers will be able to be deposited on the hair by dilution and precipitation during rinsing, whether they are applied in the presence or absence of electrolytes and/or surfactants.

The polyampholytic polymers of the present invention are preferably chosen from the group consisting of:
(1) polymers of the following formula:

$$-(A)_{x_1}-(B)_y-(C)_{x_2}-$$
$$\quad\quad|\quad\quad\quad\quad\quad\quad|$$
$$\quad D^{(-)},X^{(+)}\quad\quad\quad E^{(+)},Y^{(-)}$$

(I)

in which:
A— denotes a group resulting from the copolymerization of a monomer containing ethylenic unsaturation and bearing a group $D^{(-)}$;
$D^{(-)}$ denotes an anionic group chosen from the group consisting of:
  (i) $-COO^{\ominus}$;
  (ii) $-SO_3^{\ominus}$;
  (iii) $-PO_3^{2-}$;
  (iv) $-HPO_3^{\ominus}$;
X+ denotes a cation derived from the neutralization of the groups D by an inorganic or organic base;
B— is a group resulting from the copolymerization of at least one hydrophobic or hydrophilic, preferably relatively non-polar, monomer containing ethylenic unsaturation;
C— is a group resulting from the copolymerization of a monomer containing ethylenic unsaturation and bearing a group $-E^{(+)}$;
$E^{(+)}$ denotes a cationic group chosen from the group consisting of:

(i)
$$\quad\quad R_1$$
$$\quad\quad|$$
$$-N^{\oplus}-R_2$$
$$\quad\quad|$$
$$\quad\quad R_3$$

in which $R_1$, $R_2$ and $R_3$, which may be identical or different, denote hydrogen or a linear, branched or cyclic (cycloaliphatic or aromatic) $C_1$–$C_{22}$ alkyl group;

(ii)
$$\quad\quad R_4$$
$$\quad\quad\oplus/$$
$$-S$$
$$\quad\quad\backslash$$
$$\quad\quad R_5$$

in which $R_4$ and $R_5$, which may be identical or different, denote an aliphatic, cycloaliphatic or aromatic group;

(iii)
$$\quad\quad R_6$$
$$\quad\quad|\oplus$$
$$-P-R_7$$
$$\quad\quad|$$
$$\quad\quad R_8$$

in which $R_6$, $R_7$ and $R_8$, which may be identical or different, denote an aliphatic, cycloaliphatic or aromatic group;
$Y^{(-)}$ denotes an anion resulting from the neutralization of the groups E by an inorganic or organic acid or from the quaternization of the groups E;
$x_1$, $x_2$ and y respectively denote the molar percentages of group A, of group B and of group C;

$x_1$ and $x_2$ being identical or virtually identical, such that the overall charge of the polymer is close to 0 for a pH in the region of 7; the sum $x_1+x_2$ preferably being greater than or equal to 40 mol % and y preferably being less than or equal to 60 mol %.

(2) betaine homopolymers or copolymers containing at least monomers of the following formula:

(II)
$$\quad\quad\quad\quad\quad\quad\quad\quad\quad\quad\quad\quad\quad\quad\quad R_{11}$$
$$\quad\quad\quad\quad\quad\quad\quad\quad\quad\quad\quad\quad\quad\quad\quad|^+$$
$$CH_2=C-(C)_{\overline{p}}-(F)_{\overline{q}}-R_{10}-N-R_{13}-Z$$
$$\quad\quad\quad|\quad\parallel\quad\quad\quad\quad\quad\quad\quad\quad|$$
$$\quad\quad\quad R_9\quad O\quad\quad\quad\quad\quad\quad\quad R_{12}$$

in which:
$R_9$, $R_{11}$ and $R_{12}$, which may be identical or different, denote a hydrogen or a linear or branched $C_1$–$C_4$ alkyl;
Z denotes $COO^{(-)}$, $SO_3^{(-)}$ or $HPO_3^{(-)}$;
F denotes $-NH$ or O or forms, with the group $R_{10}$, an aromatic or non-aromatic $C_5$–$C_7$ ring or heterocycle;
$R_{10}$ denotes a divalent hydrocarbon-based group, in particular a $-(CH_2)-_n-$ group with n being an integer ranging from 1 to 4; a divalent oxyalkyl or divalent polyoxyalkyl group, in particular a $-(O-CH_2CH_2)_m-$ group with m being an integer ranging from 1 to 4;
$R_{10}$ can form, with $R_{11}$ and $R_{12}$, a $C_5$–$C_7$ heterocycle;
$R_{13}$ denotes a divalent hydrocarbon-based group, which may be identical to or different from $R_{10}$, in particular a $-(CH_2)-_n-$ group with n being an integer ranging from 1 to 4;
p is equal to 0 or 1 and q is equal to 0 or 1; the said polymer being other than betaine homopolymers or copolymers containing a monomer chosen from the group consisting of:
(i) the monomers of the following formula:

$$\quad\quad\quad\quad\quad\quad\quad\quad\quad\quad\quad\quad R_{11}$$
$$\quad\quad\quad\quad\quad\quad\quad\quad\quad\quad\quad\quad|$$
$$CH_2=C-C-F-R_{10}-N_+-(CH_2)n-COO$$
$$\quad\quad\quad|\quad\parallel\quad\quad\quad\quad\quad\quad\quad|$$
$$\quad\quad\quad R_9\quad O\quad\quad\quad\quad\quad\quad R_{12}$$

in which:
$R_9$, $R_{10}$, $R_{11}$, $R_{12}$, F and n have the same meanings indicated in formula (II) above;
(ii) the monomer of the following formula:

$$CH_2=CH-\underset{H}{\overset{}{\diagup\!\!\diagdown}}N_+-(CH_2)_2-COO-$$

(iii) the monomer of the following formula:

$$\quad\quad\quad\quad\quad\quad\quad\quad\quad\quad\quad\quad\quad\quad C_2H_5$$
$$\quad\quad\quad\quad\quad\quad\quad\quad\quad\quad\quad\quad\quad\quad|$$
$$CH_2=C-C-O-(OCH_2CH_2)_2-N+-(CH_2)_3-SO_3-$$
$$\quad\quad\quad|\quad\parallel\quad\quad\quad\quad\quad\quad\quad\quad\quad\quad|$$
$$\quad\quad CH_3\quad O\quad\quad\quad\quad\quad\quad\quad\quad\quad C_2H_5$$

(iv) the monomer of the following formula:

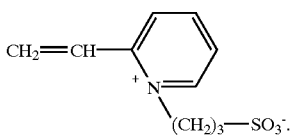

In the general formula (I) as defined above, the monomers leading, after copolymerization, to the units of structure:

when $D^{(-)}$ denotes the carboxylate function, are chosen from salts of linear, branched or cyclic carboxylic acids (which are cycloaliphatic or aromatic), such as the salts of crotonic acid, of acrylic acid, of methacrylic acid, of vinylbenzoic acid; dicarboxylic acid salts, such as the salts of maleic acid, of fumaric acid or of itaconic acid, as well as monoesters and monoamides thereof;

when $D^{(-)}$ denotes the sulphonate function, are chosen from the salts of 2-acrylamido-2 methylpropanesulphonic acid, of vinylsulphonic acid and of styrenesulphonic acid in neutralized form; the salts of 2-sulphoethyl (meth)acrylate;

when $D^{(-)}$ denotes the phosphonate function, are for example the salts of neutralized vinylphosphonic acid.

The counterion $X^{(+)}$ associated with $D^{(-)}$ generally results from the neutralization of the group D by an inorganic base such as NaOH or KOH or an organic base such as an amine or an amino alcohol.

In the general formula (I), the monomers leading to the units of structure —B— are chosen from hydrophilic or hydrophobic monomers containing ethylenic unsaturation, which are more particularly relatively nonpolar, and are chosen such that the final polymer is not soluble in water in the absence of electrolyte and/or surfactant.

By way of example, mention may be made of vinyl monomers such as linear, branched or cyclic $C_1$–$C_{24}$ vinyl esters, olefins such as ethylene, styrene and its substituted derivatives; linear, branched or cyclic $C_1$–$C_{24}$ esters or amides of (meth)acrylic acid.

The monomers leading, by copolymerization, to the units —B— can be copolymerized with silicone macromers having a vinyl end function. They can also be copolymerized by monomers containing fluoro or perfluoro groups of the vinylic, allylic or (meth)acrylic type such as, for example, vinylidene fluoride, chlorotrifluoroethylene, tetrafluoroethylene; perfluoro (meth)acrylates such as perfluorohexyl or perfluorooctyl (meth)acrylate.

In the general formula (I), the monomers leading, after copolymerization, to the units of structure:

are preferably chosen from monomers of the (meth)acrylic, vinylic, allylic or diallylic type containing a tertiary amine function quaternized with an alkyl halide or a dialkyl sulphate.

Mention may be made, for example, of:
dimethylaminoethyl (meth)acrylate,
diethylaminoethyl (meth)acrylate,
dimethylaminopropyl (meth)acrylate,
dimethylaminopropyl(meth)acrylamide,
2-vinylpyridine,
4-vinylpyridine,
dimethylallylamine,
which are quaternized with an alkyl halide or a dialkyl sulphate.

The polyampholytes of formula (I) which are particularly preferred are chosen from sodium styrene sulphonate/trimethylammonioethylmethacrylate chloride copolymers and styrene sulphonate/trimethylammonio propyl(meth)acrylamide chloride copolymers.

The molecular weights of the polyampholytes can range from 500 to 50,000,000 and are preferably greater than 10,000.

The polyampholytes containing monomers of formula (II) which are particularly preferred are chosen from the group consisting of:

poly 1-vinyl-2-(3-sulphopropyl)imidazolium hydroxide (J. C. Salamone, Polymer 1978, vol. 19, p. 1157);

poly 1-vinyl-3-(3-sulphopropyl)imidazolium hydroxide;

poly 1-vinyl-3-(4-sulphobutyl)imidazolium hydroxide;

poly 1-vinyl-2-methyl-3-(4-sulphobutyl)imidazolium hydroxide;

poly 2-methyl-5-vinyl-1-(3-sulphopropyl)pyridinium hydroxide;

poly 4-vinyl-1-(3-sulphopropyl)pyridinium hydroxide;

polydimethyl(2-methacryloxyethyl)(3-sulphopropyl) ammonium hydroxide;

polydiethyl(2-methacryloxyethoxy-2-ethyl)(3-sulphopropyl)ammonium hydroxide;

poly 4-vinylpyridinium methanecarboxybetaine;

poly 4-vinyl-4-(sulphobutyl)pyridinium hydroxide;

poly N-(3-sulphopropyl)-N-methacrylamidopropyl-N,N-dimethylalmonium betaine.

These betaine polymers are cited in the Encyclopedia of Polymer Science and Engineering—Second Edition—vol. 11, p. 517.

The polyampholytes of formula (I) can be synthesized by direct solution copolymerization in water with or without electrolyte, by solution polymerization in water/organic solvent medium. They can be obtained by precipitation copolymerization or dispersion polymerization in a water/organic solvent medium.

The general methods for polymerizing these polymers are described in the Encyclopedia of Polymer Science and Engineering, Second Edition, vol. 11, p. 521, Wiley Interscience.

They can also be obtained by reverse emulsion polymerization in the presence of water and of an organic solvent according to the process described in the article by J. M. Corpart and F. Candau, Macromolecules, vol. 26, No. 6, p. 1333, 1993.

They can also be obtained by "micellar" copolymerization in water according to a process described in the article I. Lacik, Polymer, (1995), 36 (16), 3197–3211.

When the polymerization is carried out in solution in water, a water-soluble initiator such as sodium persulphate or potassium persulphate or a redox system is preferably used.

When the polymerization is carried out in organic or aqueous-organic medium, organic initiators can also be used. The presence of a transfer agent in the polymerization medium may be necessary in order to control the final molecular weight.

The monomers constituting the polyampholytes of the invention are preferably already neutralized and/or quaternized. When the process is performed with preneutralized monomers dissolved in water, self-neutralization between the anionic and cationic groups is observed during the polymerization; this can result in a precipitation of the polymer formed.

When the process is performed in medium diluted in water, total or partial expulsion of the counterions $X^+$ and $Y^-$ in the aqueous solution is observed during the polymerization.

The polyampholytes of formula (I) can also be obtained by direct polymerization of the pair of monomer ions:

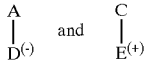

according to the method described by J. C. Salamone in the article taken from J. Macromol. Sc. Chem. A22 (5–7) pp. 653–664 (1985).

The polyampholytic polymers of formula (II) can be obtained by synthesis of the prebetainized monomer by carrying out a quaternization reaction followed by a polymerization. They can also be obtained by preparing the polymer containing amine groups, followed by quaternization.

The polyampholytic polymers of the invention are present in the compositions of the invention in proportions preferably ranging from 0.01 to 20% by weight, and more particularly from 0.1 to 10% by weight, relative to the total weight of the composition.

The aqueous compositions of the invention can also contain inorganic or organic electrolytes which allow the polyampholytic polymers to be dissolved.

The electrolytes used are preferably inorganic water-soluble salts such as alkali metal salts, alkaline-earth metal salts or aluminium salts of hydrochloric, sulphuric or nitric acid or of an organic acid such as citric acid, lactic acid or tartaric acid. The electrolytes which are particularly preferred are chosen from potassium sulphate, sodium sulphate, magnesium sulphate, calcium nitrate, aluminium nitrate, magnesium nitrate, sodium chloride, potassium chloride, aluminium chloride, potassium carbonate, sodium carbonate, aluminium carbonate and sodium citrate.

They are present in proportions ranging from 0.1 to 30% by weight, and more preferably from 1 to 10% by weight, relative to the total weight of the composition.

The pH of the aqueous compositions in accordance with the invention is preferably adjusted to between 3 and 11, and more particularly between 5 and 9, using basifying or acidifying agents or buffers.

When they are in the form of a shampoo, in particular, the compositions according to the invention comprise a washing base, generally an aqueous one. This surfactant base can also serve to dissolve the polyampholyte(s) in the aqueous medium.

The surfactant(s) forming the washing base can be chosen, indifferently, alone or as mixtures, from anionic, amphoteric, nonionic, zwitterionic and cationic surfactants.

The minimum amount of washing base is that which is just sufficient to give the final composition a satisfactory foaming and/or detergent power and/or to dissolve the polyampholytes present in the composition.

Thus, according to the invention, the washing base can represent from 4% to 30% by weight, preferably from 10% to 25% by weight and even more preferably from 12% to 20% by weight, of the total weight of the final composition.

The surfactants which are suitable for carrying out the present invention are, in particular, the following:

(i) Anionic Surfactant(s):

In the context of the present invention, their nature is not really a critical feature.

Thus, by way of example of anionic surfactants which can be used, alone or as mixtures, in the context of the present invention, mention may be made in particular (non-limiting list) of salts (in particular alkali metal salts, especially sodium salts, ammonium salts, amine salts, amino alcohol salts or magnesium salts) of the following compounds: alkyl sulphates, alkyl ether sulphates, alkyl amidoether sulphates, alkylarylpolyether sulphates, monoglyceride sulphates, alkyl sulphonates, alkyl phosphates, alkylamide sulphonates, alkylaryl sulphonates, α-olefin sulphonates, paraffin sulphonates; alkyl sulphosuccinates, alkyl ether sulphosuccinates, alkylamide sulphosuccinates; alkyl sulphosuccinamates; alkyl sulphoacetates; alkyl ether phosphates; acyl sarcosinates; acyl isethionates and N-acyl taurates, the alkyl or acyl radical of all of these different compounds preferably containing from 12 to 20 carbon atoms and the aryl radical preferably denoting a phenyl or benzyl group. Among the anionic surfactants which can also be used, mention may also be made of fatty acid salts such as oleic, ricinoleic, palmitic and stearic acid salts, coconut oil acid or hydrogenated coconut oil acid; acyl lactylates in which the acyl radical contains 8 to 20 carbon atoms. It is also possible to use weakly anionic surfactants, such as alkyl D-galactosiduronic acids and their salts, as well as polyoxyalkylenated carboxylic ether acids and their salts, in particular those containing from 2 to 50 ethylene oxide groups, and mixtures thereof. The anionic surfactants of the polyoxyalkylenated carboxylic ether acid or salt type are, in particular, those which correspond to formula (I) below:

in which:

R₁ denotes an alkyl or alkylaryl group and n is an integer or decimal (average value) which can range from 2 to 24 and preferably from 3 to 10, the alkyl radical having between 6 and 20 carbon atoms approximately, and aryl preferably denoting phenyl, A denotes H, ammonium, Na, K, Li or Mg or a monoethanolamine or triethanolamine residue. Mixtures of compounds of formula (1), in particular mixtures in which the groups R₁ are different, can also be used.

Compounds of formula (1) are sold, for example, by the company Chem Y under the names Akypos (NP40, NP70, OP40, OP80, RLM25, RLM38, RLMQ38 NV, RLM 45, RLM 45 NV, RLM 100, RLM 100 NV, RO20, RO 90, RCS 60, RS 60, RS 100, RO 50) or by the company Sandoz under the names Sandopan (DTC Acid, DTC).

(ii) Nonionic Surfactant(s):

The nonionic surfactants are also compounds that are well known per se (see in particular in this respect "Handbook of Surfactants" by M. R. Porter, published by Blackie & Son (Glasgow and London), 1991, pp. 116–178) and, in the context of the present invention, their nature is not a critical feature. Thus, they can be chosen in particular from (non-limiting list) polyethoxylated, polypropoxylated or polyglycerolated fatty acids, alkylphenols, α-diols or alcohols having a fatty chain containing, for example, 8 to 18 carbon atoms, it being possible for the number of ethylene oxide or propylene oxide groups to range in particular from 2 to 50 and for the number of glycerol groups to range in particular from 2 to 30. Mention may also be made of copolymers of ethylene oxide and of propylene oxide, condensates of ethylene oxide and of propylene oxide with fatty alcohols; polyethoxylated fatty amides preferably having from 2 to 30 mol of ethylene oxide, polyglycerolated fatty amides containing on average 1 to 5, and in particular 1.5 to 4, glycerol groups; polyethoxylated fatty amines preferably having 2 to 30 mol of ethylene oxide; oxyethylenated fatty acid esters of sorbitan having from 2 to 30 mol of ethylene oxide; fatty acid esters of sucrose, fatty acid esters of polyethylene glycol, alkylpolyglycosides, N-alkylglucamine derivatives, amine oxides such as $(C_{10}-C_{14})$alkylamine oxides or N-acylaminopropylmorpholine oxides. It will be noted that the alkylpolyglycosides constitute nonionic surfactants that are particularly suitable in the context of the present invention.

(iii) Amphoteric or Zwitterionic Surfactant(s):

The amphoteric or zwitterionic surfactants, whose nature is not a critical feature in the context of the present invention, can be, in particular (nonlimiting list), aliphatic secondary or tertiary amine derivatives in which the aliphatic radical is a linear or branched chain containing 8 to 18 carbon atoms and containing at least one water-solubilizing anionic group (for example carboxylate, sulphonate, sulphate, phosphate or phosphonate); mention may also be made of $(C_8-C_{20})$ alkylbetaines, sulphobetaines, $(C_8-C_{20})$ alkylamido $(C_1-C_6)$ alkylbetaines or $(C_8-C_{20})$ alkylamido $(C_1-C_6)$ alkylsulphobetaines.

Among the amine derivatives, mention may be made of the products sold under the name Miranol, as described in U.S. Pat. Nos. 2,528,378 and 2,781,354 and classified in the CTFA dictionary, 3rd edition, 1982, under the names Amphocarboxyglycinates and Amphocarboxypropionates, with the respective structures:

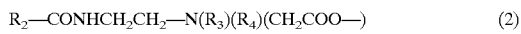

$$R_2-CONHCH_2CH_2-N(R_3)(R_4)(CH_2COO-) \quad (2)$$

in which: $R_2$ denotes an alkyl radical of an acid $R_2$—COOH present in hydrolysed coconut oil, a heptyl, nonyl or undecyl radical, $R_3$ denotes a β-hydroxyethyl group and $R_4$ denotes a carboxymethyl group; and

$$R_2-CONHCH_2CH_2-N(B)(C) \quad (3)$$

in which:

B represents —$CH_2CH_2OX'$, C represents —$(CH_2)_z$—Y', with z=1 or 2,

X' denotes the —$CH_2CH_2$—COOH group or a hydrogen atom,

Y' denotes —COOH or the —$CH_2$—CHOH—$SO_3H$ radical, $R_2$, denotes an alkyl radical of an acid $R_9$—COOH present in coconut oil or in hydrolysed linseed oil, an alkyl radical, in particular a $C_7$, $C_9$, $C_{11}$ or $C_{13}$ alkyl radical, a $C_{17}$ alkyl radical and its iso form, an unsaturated $C_{17}$ radical.

By way of example, mention may be made of the cocoamphocarboxyglycinate sold under the trade name Miranol $C_2M$ concentrate by the company Miranol.

(iv) Cationic Surfactants:

Among the cationic surfactants, whose nature, in the context of the present invention, is not a critical feature, mention may be made in particular (non-limiting list) of: salts of optionally polyoxyalkylenated primary, secondary or tertiary fatty amines; quaternary ammonium salts such as tetraalkylammonium, alkylamidoalkyltrialkylammonium, trialkylbenzylammonium, trialkylhydroxyalkylammonium or alkylpyridinium chlorides or bromides; imidazoline derivatives; or amine oxides of cationic nature.

The cosmetically or dermatologically acceptable medium of the compositions of the invention is preferably water or an aqueous-alcoholic solution of a lower alcohol such as ethanol, isopropanol or butanol.

Needless to say, the compositions according to the invention can also contain adjuvants that are common in the field of hair compositions, such as, for example, fragrances, preserving agents, sequestering agents, thickeners, softeners, foam modifiers, dyes, pearlescent agents, moisturizers, antidandruff agents, antiseborrhoeic agents, vitamins, sunscreens and the like.

Needless to say, a person skilled in the art will take care to select this or these optional complementary compounds and/or the amounts thereof such that the advantageous properties intrinsically associated with the composition in accordance with the invention are not, or are not substantially, adversely affected by the addition(s) envisaged.

These compositions can be in the form of relatively thickened liquids, creams or gels and they are mainly suitable for washing, caring for and/or styling the hair. They can also be in the form of rinse-out lotions.

Another subject of the invention consists of a non-therapeutic treatment process for the hair, characterized in that a composition as defined above is applied directly to wet hair and, after optionally leaving it on the hair for a period of time, the hair is rinsed with water; the said process can be repeated several times.

As indicated above, the compositions according to the invention give the hair, after rinsing, a noteworthy styling effect which is manifested in particular by an ease of styling and of maintenance, as well as substantially improved disentangling of wet hair.

The examples which follow serve to illustrate the present invention without, however, being limiting in nature.

EXAMPLES

Preparation Example 1

Synthesis of the Copolymer of Sodium Styrenesulplonate and of Trimethylammonioethyl Methacrylate Chloride (50/50 mol %) of Formula (I)

49.8 g of sodium styrenesulphonate powder are introduced into a reactor with a central mechanical stirrer, a condenser, a thermometer and a nitrogen sparge. 63.63 g of an aqueous solution with a trimethylammonioethyl methacrylate chloride solids content of 78.9% are then introduced. Next, 300 g of deionized water plus 2 g of potassium persulphate (polymerization initiator) are introduced. All of these additions are carried out at room temperature.

The reaction medium is stirred at 400 rev/min in order to obtain dissolution and homogenization.

The mixture is sparged with nitrogen. The medium is heated to 72° C. and this temperature is maintained, with stirring, for 24 hours.

At the end of the polymerization, the reaction medium is cooled to room temperature. The medium is cloudy but the polymer does not precipitate.

The polymer is purified by precipitation of the synthesis solution in 5 l of deionized water. The precipitate is recovered. It is dried in an oven under vacuum at 45° C. until a constant weight is obtained.

The elemental analysis is in agreement with that of the theoretical polymer. The yield obtained is 85%.

The polymer thus obtained is insoluble in water at 1% by weight.

It can be dissolved in water at a concentration of 1% by adding a minimum amount of 3.85% by weight of NaCl.

It can also be dissolved in a washing base consisting of:

| | |
|---|---|
| sodium lauryl ether sulphate | 15% by weight |
| cocoylbetaine | 3% by weight |
| water qs | 100% by weight | at a concentration of 1% by weight, by adding a minimum amount of 2% NaCl.

Preparation Example 2

Synthesis of the Copolymer of Sodium Styrenesulphonate and of Trimethylammoniopropylmethacrylamide Chloride (50/50 mol %)

The process is performed under the same conditions as those used in Example 1, using 48.3 g of sodium styrenesulphonate, 98.48 g of an aqueous solution with a trimethylammoniopropylmethacrylamide chloride solids content of 52.5%, 500 g of deionized water and 2 g of ammonium persulphate.

The elemental analysis is in agreement with that of the theoretical polymer. The yield obtained is 91%.

The polymer thus obtained is insoluble in water at a concentration of 1% by weight. It can be dissolved in water at this same concentration in the presence of at least 5.66% of the weight of NaCl.

It can be dissolved in the washing base of Example 1 at this same concentration in the presence of at least 4.76% by weight of NaCl.

Preparation Example 3

Synthesis of the Copolymer of 2-Acrylamido-2-methylpropanesulphonic Acid and of Trimethylammonioethyl Methacrylate Chloride (50/50 mol %)

The process is performed in the same reactor as that used in Example 1, using 47.42 g of 2-acrylamido-2-methylpropanesulphonic acid and 60.25 g of an aqueous solution with a trimethylammonioethyl methacrylate chloride solids content of 78.9%.

Before introducing the quaternary monomer, the sulphonic monomer is introduced into the reactor, followed by 200 g of deionized water for dissolution and homogenization at room temperature.

The sulphonic monomer is neutralized by adding 26.3 g of 35% NaOH, with stirring at room temperature. The quaternary monomer is then introduced and 150 g of deionized water and 2 g of ammonium persulphate are added. The mixture is stirred, sparged with nitrogen and heated at 72° C. for 24 hours. A cloudy solution is obtained. This concentrated solution precipitates in water but the precipitate is recovered and purified by precipitation of the synthesis solution in 5 l of ethanol. The precipitate is dried in an oven until a constant weight is obtained. The yield obtained is 85%.

The polymer obtained dissolves directly at a concentration of 1% by weight in the washing base of Example 1. Beyond 4% by weight in this washing base, NaCl needs to be added in order to maintain the solubilization.

Preparation Example 4

Synthesis of the Copolymer of the Sodium Salt of 2-Acrylamido-2-methylpropanesulphonic Acid and of Trimethylammoniopropylmethacrylamide Chloride (50/50 mol %)

An aqueous solution with a sodium salt of 2-acrylamido-2-methylpropanesulphonic acid solids content of 49.15% is prepared by neutralizing the acid with a stoichiometric amount of NaOH.

103.68 g of the said aqueous solution are introduced into a reactor identical to that of Example 1, followed by 93.43 g of an aqueous solution with a trimethylammoniopropylmethacrylamide chloride solids content of 52.5%. 300 g of deionized water and 2 g of ammonium persulphate are then added.

The process is then performed under the same conditions as those used in Example 3. The yield obtained is 88%.

The polymer thus obtained is insoluble in water at a concentration of 1% and dissolves at the same concentration in the presence of at least 3.62% NaCl. It dissolves directly at the same concentration in the washing base of Example 1. Beyond 5.5% by weight, an electrolyte needs to be added in order to maintain its dissolution.

Example A

Shampoo

| | |
|---|---|
| Alkylpolyglucoside sold under the name APG 300 by Henkel | 15 g |
| Sodium lauryl ether sulphate containing 2 mol of ethylene oxide | 18 g AM |
| Polyethylene glycol dioleate (55 EO) and propylene glycol dioleate/water, sold by the company Goldschmidt under the name Ansil 141 | 5 g |
| Polymer of Example 1 | 1 g AM |
| Polydimethylsiloxane containing aminoethyl, aminopropyl and α, ω-silanol groups, at 30% in a nonionic microemulsion, sold under the name Silbione 71827 by Rhône-Poulenc | 2 g AM |
| NaCl | 2 g |
| Preserving agents, fragrances | |
| Water qs | 100 g |
| pH adjusted to 5 with HCl | |

Example B

Shampoo

| | |
|---|---|
| Sodium lauryl sulphate | 18 g AM |
| Cocoylbetaine | 3 g AM |
| Polymer of Example 1 | 1 g AM |
| Polydimethylsiloxane sold under the name Mirasil DM 500,000 by Rhône-Poulenc | 2 g AM |
| 1-(Hexadecyloxy)-2-octadecanol/cetyl alcohol mixture (47/53) | 2.5 g |
| Coconut acid monoisopropanolamide | 1 g |
| NaCl | 2 g |
| Preserving agents, fragrances | |
| Water qs | 100 g |
| pH adjusted to 7.2 with NaOH | |

After application and rinsing, this shampoo gives very good disentangling to wet hair and makes dry hair supple and flowing.

Example C
Shampoo

| | |
|---|---|
| Sodium lauryl ether sulphate containing 2 mol of ethylene oxide | 10 g AM |
| Ammonium lauryl sulphate | 5 g AM |
| Polymer of Example 1 | 0.5 g AM |
| Polyphenyltrimethylsiloxysiloxane sold under the name Abil AV 1000 by the company Goldschmidt | 2 g |
| Lauric diethanolamide | 2 g |
| Ethylene glycol distearate | 2 g |
| NaCl | 3 g |
| Preserving agents, fragrances | |
| Water qs | 100 g |
| pH adjusted to 7.8 with NaOH | |

This shampoo has good washing properties and gives, after application and rinsing, very good disentangling and improves the manageability and hold of dried hair.

Example D
Shampoo

| | |
|---|---|
| Sodium lauryl ether sulphate containing 2 mol of ethylene oxide | 14 g AM |
| Polymer of Example 1 | 2 g AM |
| Mixture of polydimethylsiloxane/trimethyl-siloxysilicate sold under the name DC 593 Fluid by Dow Corning | 0.5 g |
| Glycol distearate ($C_{16}$–$C_{18}$; 30/70) | 2.5 g |
| Coconut acid monoisopropanolamide | 0.8 g |
| NaCl | 3 g |
| Preserving agents, fragrances | |
| Water qs | 100 g |
| pH adjusted to 6 with HCl | |

Example E
Shampoo

| | |
|---|---|
| Xanthan gum | 1 g |
| Polymer of Example 1 | 2 g AM |
| Polydimethyl/methylcetyl/methylsiloxane sold under the name Abil EM 90 by Goldschmidt | 2 g |
| NaCl | 3 g |
| Behenyltrimethylammonium chloride sold under the name Genamin KDMF by Hoechst | 2 g |
| Preserving agents, fragrances | |
| Water qs | 100 g |
| pH = 4 (spontaneous) | |

After application and rinsing, this conditioner gives very good disentangling of wet hair and a good styling effect.

What is claimed is:

1. A composition for treating keratin substances, said composition comprising, in a cosmetically and/or dermatologically acceptable aqueous medium:
   (a) at least one non-volatile, water-insoluble polyorganosiloxane having a viscosity of greater than $3 \times 10^{-5}$ m²/s; and
   (b) at least one polyampholytic polymer comprising, in the chain or in a side position relative to the chain, equimolar amounts, or virtually equimolar amounts, of negative charges and positive charges; said polyampholytic polymer being insoluble in water at a concentration of greater than or equal to 0.1% by weight and at 20° C. and said polyampholytic polymer being other than betaine homopolymers or copolymers containing a monomer selected from:
   (i) a monomer of the following formula:

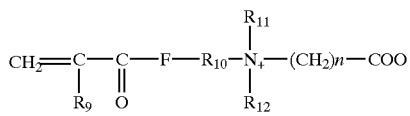

in which:
   $R_9$, $R_{11}$ and $R_{12}$ are identical or different and denote a hydrogen or an alkyl radical;
   $R_{10}$ denotes a group —$(CH_2)_n$— or —(O—$CH_2$—$CH_2)_m$—;
   F denotes NH or O; and
   m and n are integers ranging from 1 to 4 inclusive;
   (ii) a monomer of the following formula:

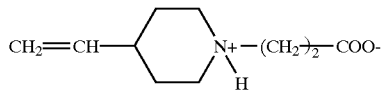

(iii) a monomer of the following formula:

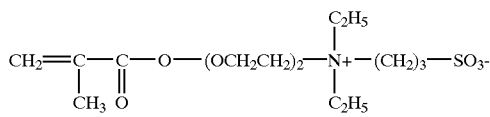

and (iv) a monomer of the following formula:

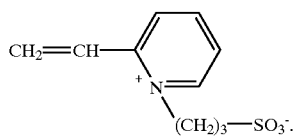

2. A composition according to claim 1, wherein said at least one polyorganopolysiloxane has a viscosity of greater than $5 \times 10^{-5}$ m²/s.

3. A composition according to claim 2, wherein said at least one polyorganopolysiloxane has a viscosity of greater than $10 \times 10^{-5}$ m²/s.

4. A composition according to claim 1, wherein said at least one polyorganosiloxane is:
   (i) a polyalkylsiloxane;
   (ii) a polyarylsiloxane;
   (iii) a polyalkylarylsiloxane;
   (iv) a silicone gum;
   (v) a silicone resin;
   (vi) a polyorganosiloxane containing in its general structure one or more organofunctional groups directly attached to the siloxane chain or attached via a hydrocarbon-based radical;
   (vii) a block copolymer having a polysiloxane-polyoxyalkylene linear block as a repeating unit;
   (viii) a grafted silicone polymer comprising a non-silicone organic skeleton, comprising an organic main chain formed from organic monomers not containing silicone, onto which is grafted, within said chain, at least one polysiloxane macromonomer;

(ix) a grafted silicone polymer comprising a polysiloxane skeleton, grafted with non-silicone organic monomers, comprising a polysiloxane main chain onto which is grafted, within said chain, at least one organic macromonomer not containing silicone; or (x) mixtures thereof.

5. A composition according to claim 1, wherein said at least one polyorganosiloxane is a grafted silicone polymer comprising a non-silicone organic skeleton, comprising an organic main chain formed from organic monomers not containing silicone, onto which is grafted, within said chain as well as on at least one of its ends, at least one polysiloxane macromonomer.

6. A composition according to claim 1, wherein said at least one polyorganosiloxane is a grafted silicone polymer comprising a polysiloxane skeleton, grafted with non-silicone organic monomers, comprising a polysiloxane main chain onto which is grafted, within said chain as well as on at least one of its ends, at least one organic macromonomer not containing silicone.

7. A composition according to claim 4, wherein said at least one polyalkylsiloxane is:

a linear polydimethylsiloxane containing trimethylsilyl end groups, a linear polydimethylsiloxane containing hydroxydimethylsilyl end groups, or a mixture thereof.

8. A composition according to claim 4, wherein said at least one polyorganosiloxane is a silicone gum, and further wherein said silicone gum is a polydi-organopolysiloxane with a molecular mass ranging from 200,000 to 1,000,000, said silicone gum being present alone or as a mixture in a solvent selected from volatile silicones, polydimethylsiloxane oils, polyphenylmethylsiloxane oils, isoparaffins, methylene chloride, pentane, dodecane, tridecane and tetradecane, and mixtures thereof.

9. A composition according to claim 8, wherein said silicone gum is:

polydimethylsiloxane, poly{(dimethylsiloxane)/(methylvinylsiloxane)}, poly{(dimethylsiloxane)/(diphenylsiloxane)}, poly{(dimethylsiloxane)/(phenylmethylsiloxane)}, or poly{(dimethylsiloxane)/(diphenylsiloxane)/(methylvinylsiloxane)}.

10. A composition according to claim 8, wherein said silicone gum is:

(a) a mixture formed from a polydimethylsiloxane hydroxylated at the end of the chain and from a cyclic polydimethylsiloxane;

(b) a mixture formed from a polydimethylsiloxane gum with a cyclic silicone; or (c) a mixture of two polydimethylsiloxanes (PDMS) of different viscosity.

11. A composition according to claim 4, wherein said at least one polyorganosiloxane is a siloxane system containing the units $R_2SiO_{2/2}$, $RSiO_{3/2}$, and $SiO_{4/2}$, in which R denotes a hydrocarbon-based group comprising 1 to 6 carbon atoms or a phenyl group.

12. A composition according to claim 4, wherein said at least one polyorganosiloxane is a polyorganosiloxane containing in its general structure one or more organofunctional groups directly attached to the siloxane chain or attached via a hydrocarbon-based radical and is selected from those containing:

(a) a polyethylenoxy and/or polypropylenoxy group;

(b) a (per)fluoro group;

(c) a hydroxyacylamino group;

(d) a thiol group;

(e) a carboxylate group;

(f) a hydroxyl group;

(g) an alkoxy group;

(h) an acyloxyalkyl group;

(i) a substituted or unsubstituted amine group;

(j) a quaternary ammonium group;

(k) an amphoteric or betaine group; and (l) a bisulphite group.

13. A composition according to claim 12, wherein said polyethylenoxy and/or polypropylenoxy group contain an alkyl group.

14. A composition according to claim 4, wherein said at least one polyorganosiloxane is a linear block copolymer corresponding to the formula:

in which

R and R' are identical or different and represent a monovalent hydrocarbon-based radical containing no aliphatic unsaturation, n is an integer ranging from 2 to 4, a is an integer greater than or equal to 5, b is an integer greater than or equal to 4, c is an integer greater than or equal to 4, Y represents a divalent organic group which is linked to the adjacent silicon atom via a carbon-silicon bond and to a polyoxyalkylene block via an oxygen atom, the average molecular weight of each siloxane block $(Y(R_2SiO)_a R'_2SiYO)$ ranges from about 400 to about 10,000, and the average molecular weight of each polyoxyalkylene block $(C_nH_{2n}O)_b$ ranges from about 300 to about 10,000, said siloxane blocks represent from about 10% to about 95% of the weight of the block copolymer, and the average molecular weight of the block copolymer is at least 3000.

15. A composition according to claim 14, wherein R and R' are independently a methyl, ethyl, propyl, butyl, pentyl, hexyl, octyl, decyl, dodecyl, phenyl, naphthyl, benzyl, phenylethyl, tolyl, xylyl or cyclohexyl radical.

16. A composition according to claim 14, wherein Y is —R''—, —R''—CO—, —R''—NHCO—, R''—NH—CONH—R'''NHCO or —R''—OCONH—R'''—NHCO—, where R'' represents an ethylene, propylene or butylene radical, and R''' represents a group —$C_6H_4$—, —$C_6H_4$—$C_6H_4$—, —$C_6H_4$—$CH_2$—$C_6H_4$— or —$C_6H_4$—$CH(CH_3)_2$—$C_6H_4$—.

17. A composition according to claim 14, wherein said polysiloxane-polyoxyalkylene linear block copolymer is selected from copolymers of formula:

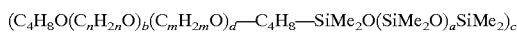

where Me denotes methyl, m and n are integers from 2 to 4, a and c are integers greater than or equal to 4, b and d are integers greater than or equal to 0, and the sum of b+d is greater than or equal to 4.

18. A composition according to claim 17, wherein said polysiloxane-polyoxyalkylene linear block copolymer has, as a repeating unit, a unit of structure:

$$(-(SiMe_2O)_xSiMe_2-C_4H_8O-(C_2H_4O)_y-(C_3H_6O)_z-C_4H_8-)$$

where x is a number ranging from 5 to 15 inclusive, y is a number ranging from 15 to 30 inclusive and z is a number ranging from 20 to 40 inclusive.

19. A composition according to claim 14, wherein the block copolymer is selected from:

$(((CH_3)_2SiO)_{41}(CH_3)_2SiCH_2CH(CH_3)CH_2-O(C_2H_4O)_{18}-(C_3H_6O)_{33}CH_2CH(CH_3)CH_2)_{16.1}$ $(((CH_3)_2SiO)_{31}(CH_3)_2SiCH_2CH(CH_3)CH_2-O(C_2H_4O)_{20}-(C_3H_6O)_{29}CH_2CH(CH_3)CH_2)_{13.3}$ $(((CH_3)_2SiO)_9(CH_3)_2SiCH_2CH(CH_3)CH_2-O(C_2H_4O)_{20}-(C_3H_6O)_{29}CH_2CH(CH_3)CH_2)_{26.3}$ $(((CH_3)_2SiO)_{16}(CH_3)_2SiCH_2CH(CH_3)CH_2-O(C_2H_4O)_{18}-(C_3H_6O)_{20}CH_2CH(CH_3)CH_2)_{21.5}$ and $(((CH_3)_2SiO)_9(CH_3)_2SiCH_2CH(CH_3)CH_2-O(C_2H_4O)_5-CH_2CH(CH_3)CH_2)_{4.8}$.

20. A composition according to claim 1, wherein said at least one polyorganosiloxane is present in an amount ranging from 0.001to 20% by weight relative to the total weight of the composition.

21. A composition according to claim 20, wherein said at least one polyorganosiloxane is present in an amount ranging from 0.01to 10% by weight relative to the total weight of the composition.

22. A composition according to claim 1, wherein said at least one polyampholytic polymer is a polymer corresponding to the following formula (I):

$$-(A-)_{x_1}-(B-)_y-(C-)_{x_2}- \quad (I)$$
$$\phantom{xxx}|\phantom{xxxxxxxxxxxxx}|$$
$$D^{(-)},X^{(+)}\phantom{xxxxxx}E^{(+)},Y^{(-)}$$

in which:
A— denotes a group resulting from the copolymerization of at least one monomer containing ethylenic unsaturation and bearing a group $D^{(-)}$;
$D^{(-)}$ denotes an anionic group selected from:
  (i) $-COO^{\ominus}$;
  (ii) $-SO_3^{\ominus}$;
  (iii) $-PO_3^{2-}$; and
  (iv) $-HPO_3^{\ominus}$;
X+ denotes a cation derived from the neutralization of the group $D^{(-)}$ by an inorganic or organic base;
B— denotes a group resulting from the copolymerization of at least one hydrophobic or hydrophilic monomer containing ethylenic unsaturation;
C— is a group resulting from the copolymerization of at least one monomer containing ethylenic unsaturation and bearing a group —E(+);
E(+) denotes a cationic group selected from:

(i)
$$-\overset{R_1}{\underset{R_3}{\overset{|}{\underset{|}{N^{\oplus}}}}}-R_2$$

in which $R_1$, $R_2$ and $R_3$ are identical or different and denote hydrogen or a linear, branched, cycloaliphatic or aromatic $C_1-C_{22}$ alkyl group;

(ii)
$$-\overset{R_4}{\underset{R_5}{\overset{|}{\underset{\backslash}{S^{\oplus}}}}}$$

in which $R_4$ and $R_5$ are identical or different and denote an aliphatic, cycloaliphatic or aromatic group; and (iii)
$$-\overset{R_6}{\underset{R_8}{\overset{|}{\underset{|}{P^{\oplus}}}}}-R_7$$

in which $R_6$, $R_7$ and $R_8$ are identical or different and denote an aliphatic, cycloaliphatic or aromatic group;
$Y^{(-)}$ denotes an anion resulting from the neutralization of said group E(+) by an inorganic or organic acid or by quaternization of said group E(+); and $x_1$, $x_2$ and y respectively denote the molar concentration of group A, of group B and of group C, $x_1$ and $x_2$ being identical or virtually identical, such that the overall charge of the polymer is close to 0 for a pH in the region of 7.

23. A composition according to claim 22, wherein, in formula (I), the sum $x_1+x_2$ is greater than or equal to 40 mol % and y is less than or equal to 60 mol %.

24. A composition according to claim 22, wherein, in formula (I), D(-) denotes carboxylate and $$-\overset{A}{\underset{D^{(-)}}{\overset{|}{\phantom{x}}}}-$$

is a linear, branched or cyclic carboxylic acid salt; a salt of a linear, branched or cyclic dicarboxylic acid, or a monoester or monoamide thereof.

25. A composition according to claim 22, wherein, in formula (I), $D^{(-)}$ denotes sulphonate and $$-\overset{A}{\underset{D^{(-)}}{\overset{|}{\phantom{x}}}}-$$

is a salt of 2-acrylamido-2-methylpropanesulphonic acid, of vinylsulphonic acid, or of styrenesulphonic acid, or a salt of 2-sulphoethyl methacrylate.

26. A composition according to claim 22, wherein, in formula (I), $D^{(-)}$ denotes phosphonate and $$-\overset{A}{\underset{D^{(-)}}{\overset{|}{\phantom{x}}}}-$$

denotes a salt of vinylphosphonic acid.

27. A composition according to claim 22, wherein the group —B— comprises at least one monomer selected from a linear, branched or cyclic $C_1-C_{24}$ vinyl ester; an olefin; styrene and a substituted derivative thereof; and a linear, branched or cyclic $C_1-C_{24}$ ester or amide of (meth)acrylic acid.

28. A composition according to claim 22, wherein the group —B— comprises at least one monomer selected from a silicone macromer containing a vinyl end function, and vinylic, allylic and (meth)acrylic monomers bearing a fluoro or a perfluoro group.

29. A composition according to claim 22, wherein the monomer

is a (meth)acrylic, vinylic, allylic or diallylic monomer bearing a tertiary amine E quaternized with an alkyl halide or a dialkyl sulphate.

30. A composition according to claim 22, wherein the polymer of formula (I) is a copolymer of sodium styrene sulphonate/trimethylammoniopropyl (meth)acrylamide chloride or a copolymer of sodium styrene sulphonate/trimethylammonioethyl methacrylate.

31. A composition according to claim 1, wherein said at least one polyampholytic polymer contains a monomer of the following formula (II):

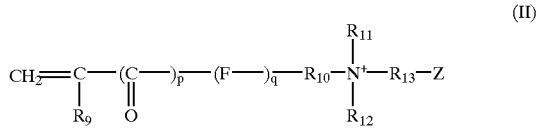

(II)

in which:

$R_9$, $R_{11}$ and $R_{12}$ are identical or different and denote a hydrogen or a linear or branched $C_1$–$C_4$ alkyl;

Z denotes $COO^{(-)}$, $SO_3^{(-)}$ or $HPO_3^{(-)}$;

F denotes —NH or O or forms, with the group $R_{10}$, an aromatic or non-aromatic $C_5$–$C_7$ ring or heterocycle;

$R_{10}$ denotes a divalent hydrocarbon-based group; a divalent oxyalkyl or divalent polyoxyalkyl group;

$R_{10}$ can form, with $R_{11}$ and $R_{12}$, a $C_5$–$C_7$ heterocycle;

$R_{13}$ denotes a divalent hydrocarbon-based group, which is identical to or different from $R_{10}$;

p is equal to 0 or 1 and q is equal to 0 or 1;

said at least one polyampholytic polymer being other than a betaine homopolymer or a copolymer containing a monomer selected from:

(i) a monomer of the following formula:

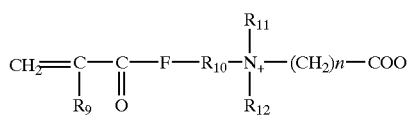

in which:
$R_9$, $R_{10}$, $R_{11}$, $R_{12}$, F and n have the same meanings indicated in formula (II) above;

(ii) a monomer of the following formula:

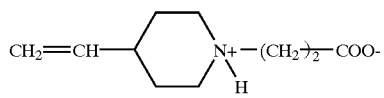

(iii) a monomer of the following formula:

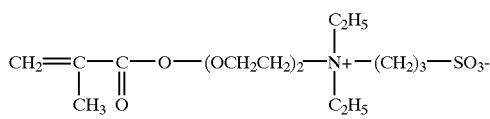

and (iv) a monomer of the following formula:

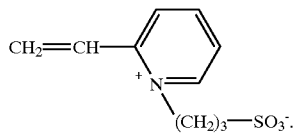

32. A composition according to claim 31, wherein, in formula (II), $R_{10}$ is:
a —$(CH_2)_n$— group where n is an integer ranging from 1 to 4 or
a —$(O—CH_2CH_2)_m$— group where m is an integer ranging from 1 to 4.

33. A composition according to claim 31, wherein, in formula (II), $R_{13}$ a —$(CH_2)_n$— group where n is an integer ranging from 1 to 4.

34. A composition according to claim 31, wherein said at least one polyampholytic polymer is:
poly 1-vinyl-2-(3-sulphopropyl)imidazolium hydroxide;
poly 1-vinyl-3-(3-sulphopropyl)imidazolium hydroxide;
poly 1-vinyl-3-(4-sulphobutyl)imidazolium hydroxide;
poly 1-vinyl-2-methyl-3-(4-sulphobutyl)imidazolium hydroxide;
poly 2-methyl-5-vinyl-1-(3-sulphopropyl)pyridinium hydroxide;
poly 4-vinyl-1-(3-sulphopropyl)pyridinium hydroxide;
polydimethyl(2-methacryloxyethyl)(3-sulphopropyl)-ammonium hydroxide;
polydiethyl(2-methacryloxyethoxy-2-ethyl)(3-sulphopropyl)-ammonium hydroxide;
poly 4-vinylpyridinium methanecarboxybetaine;
poly 4-vinyl-4-(sulphobutyl)pyridinium hydroxide; or
poly N-(3-sulphopropyl)-N-methacrylamidopropyl-N,N-dimethylammonium betaine.

35. A composition according to claim 1, wherein said at least one polyampholytic polymer is present in an amount ranging from 0.01% to 20% by weight relative to the total weight of the composition.

36. A composition according to claim 35, wherein said at least one polyampholytic polymer is present in an amount ranging from 0.1% to 10% by weight.

37. A composition according to claim 1, wherein said composition further comprises at least one inorganic or organic electrolyte.

38. A composition according to claim 37, wherein the electrolyte is present in an amount ranging from 0.1% to 30% by weight relative to the total weight of the composition.

39. A composition according to claim 38, wherein the electrolyte is present in an amount ranging from 1% to 10% by weight relative to the total weight of the composition.

40. A composition according to claim 1, wherein the pH of said composition ranges from 3 to 11.

41. A composition according to claim 1, wherein said composition further comprises a washing base comprising at least one surfactant or a mixture of surfactants selected from anionic, cationic, nonionic, amphoteric and zwitterionic surfactants.

42. A composition according to claim 41, wherein said washing base represents from 4 to 30% by weight of the total weight of the composition.

43. A composition according to claim 42, wherein the washing base represents from 10 to 25% by weight of the total weight of the composition.

44. A composition according to claim 43, wherein the washing base represents from 12 to 20% by weight of the total weight of the composition.

45. A composition according to claim 1, wherein said cosmetically or dermatologically acceptable medium comprises water or a mixture of water and a lower alcohol.

46. A composition according to claim 1, further comprising at least one adjuvant, wherein said at least one adjuvant is a fragrance, a preserving agent, a sequestering agent, a thickener, a softener, a foam modifier, a dye, a pearlescent agent, a moisturizer, an antidandruff agent, an antiseborrhoeic agent, a vitamin or a sunscreen.

47. A composition according to claim 1, said composition being in the form of a thickened liquid, lotion, cream or gel.

48. A composition according to claim 1, said composition being a rinse-out product to wash, care for and/or style the hair.

49. A non-therapeutic treatment process for the hair, said process comprising:

applying an effective amount of a composition according to claim 1 directly to the hair and rinsing the hair with water.

50. A process according to claim 49, further comprising, after applying said composition to the hair, leaving said composition on the hair for a period of time before rinsing the hair with water.

* * * * *

UNITED STATES PATENT AND TRADEMARK OFFICE
CERTIFICATE OF CORRECTION

PATENT NO. : 6,403,073 B1
DATED : June 11, 2002
INVENTOR(S) : Cauwet-Martin et al.

It is certified that error appears in the above-identified patent and that said Letters Patent is hereby corrected as shown below:

Column 18,
Line 10, in the formula, "COO" should read -- $COO^-$ --.

Column 22,
Line 26, "0for" should read -- 0 for --.

Signed and Sealed this

Fifth Day of August, 2003

JAMES E. ROGAN
*Director of the United States Patent and Trademark Office*